United States Patent
Yeh et al.

[11] Patent Number: 5,868,722
[45] Date of Patent: *Feb. 9, 1999

[54] SMOKE EVACUATION APPARATUS

[75] Inventors: Charles R. Yeh, Plantation; Paul J. Celauro, Sunrise, both of Fla.

[73] Assignee: Acuderm Inc., Fort Lauderdale, Fla.

[*] Notice: The term of this patent shall not extend beyond the expiration date of Pat. No. 5,626,586.

[21] Appl. No.: 823,869

[22] Filed: Mar. 25, 1997

Related U.S. Application Data

[63] Continuation of Ser. No. 579,615, Dec. 26, 1995, Pat. No. 5,626,568.

[51] Int. Cl.⁶ .................................................. A61M 1/00
[52] U.S. Cl. ........................................................ 604/313
[58] Field of Search ................................ 604/313–317, 604/319–320; 55/385.1, 467; 137/808; 454/188–191; 239/198, 601

[56] References Cited

U.S. PATENT DOCUMENTS

| | | | |
|---|---|---|---|
| 722,019 | 3/1903 | Hildebrantdt et al. | 604/315 |
| 765,746 | 7/1904 | Miner | 604/315 |
| 996,974 | 7/1911 | Chellis | 604/315 |
| 3,625,133 | 12/1971 | Hayashi | 454/189 |
| 4,735,603 | 4/1988 | Goodson et al. | 604/317 |
| 4,963,134 | 10/1990 | Backscheider et al. | 604/319 |
| 5,047,072 | 9/1991 | Wertz et al. | 55/1 |
| 5,626,568 | 5/1997 | Yeh et al. | 604/315 |

*Primary Examiner*—John G. Weiss
*Assistant Examiner*—David J. Cho
*Attorney, Agent, or Firm*—Rockey, Milnamow & Katz, Ltd.

[57] ABSTRACT

A smoke evacuator for use in electrosurgical and laser surgical procedures in which a source of rapidly moving fluid under pressure is introduced to a surgical site to entrain smoke and other surgical debris generated during the procedure and a collection element operated under reduced pressure. The latter is positioned adjacent to the surgical site so that the moving fluid stream entrains all of the smoke and surgical debris which is then collected in the collection element. In the preferred embodiment of the invention, the collection element includes a flared horn portion to ensure laminar flow of the fluid stream as it enters the collection element. In accordance with another embodiment of the invention, the source of fluid under pressure and the collection element are mounted on a laser surgery handpiece or probe whereby the fluid pressure source and the collection element are integral with the probe and thus the tube is repositioned as the probe is repositioned.

7 Claims, 4 Drawing Sheets

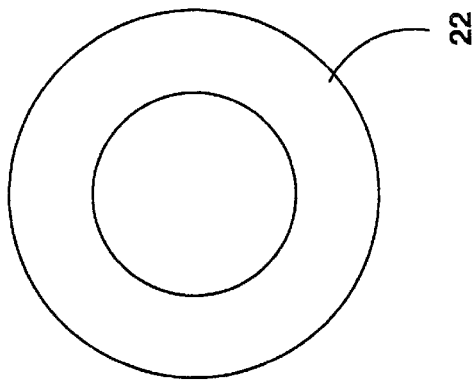
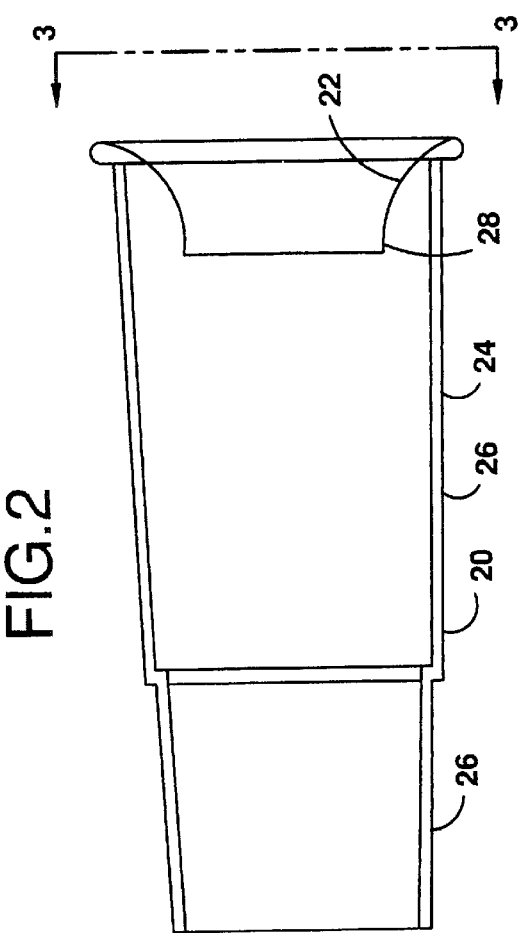
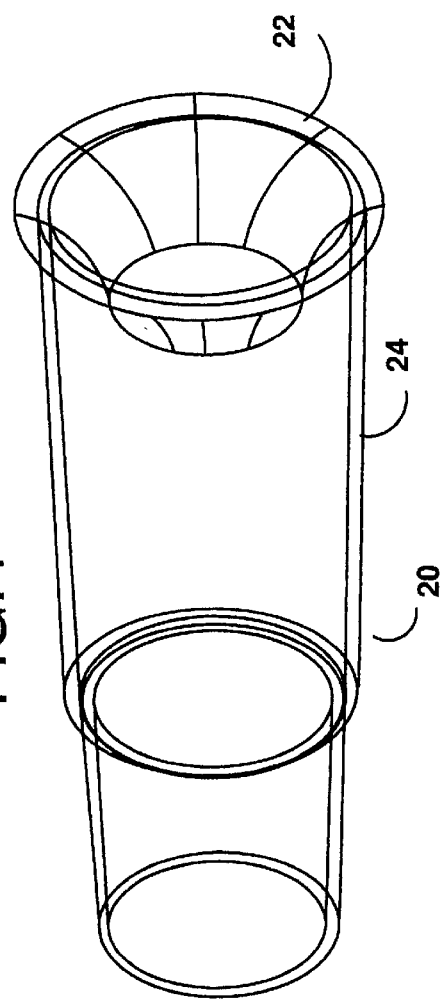

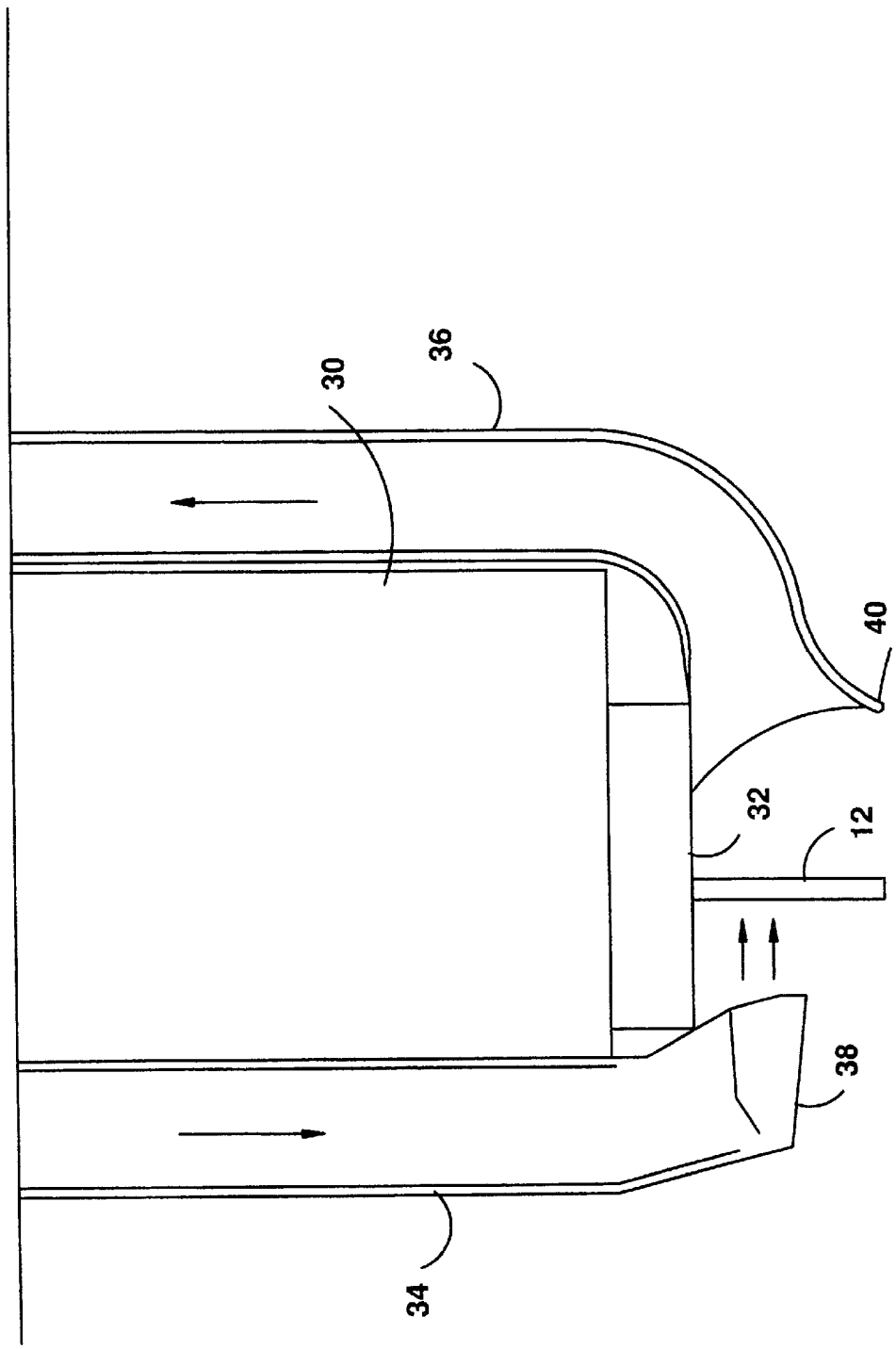

SMOKE EVACUATION APPARATUS

This is a continuation of application Ser. No. 08/579,615 filed Dec. 26, 1995, now U.S. Pat. No. 5,626,568.

BACKGROUND OF THE INVENTION

The present invention is directed to smoke evacuation apparatus, and more particularly to an improved system for use in the collection of smoke and other airborne debris generated in the course of electrosurgery and laser surgery.

Electrosurgery and laser surgery are found in more widespread use, and particularly in many types of dermatologic surgery procedures. As is well known to those skilled in the art, electrosurgery may involve the use of electrically heated needles which may be used to burn tissue from the surgical site or may involve electrodesiccation and fulguration procedures in which an electric arc is generated between a needle and surgical site.

By the same token, laser surgery is likewise gaining widespread acceptance in procedures in which a laser is used to burn and/or vaporize tissue from a surgical site. Such laser surgical techniques are becoming more widely used in a variety of dermatologic surgery operations. In both electrosurgery and laser procedures, the surgical techniques employed generate a great deal of smoke and other airborne particulate matter in the vicinity of the surgical site. Because such particulate matter itself may be pathogenic, smoke evacuation techniques have been developed to physically remove the smoke and other surgical debris from the surgical site.

A number of smoke evacuators have been developed for that purpose. One particularly successful example is the smoke evacuator described in U.S. Pat. No. 5,423,779 to Charles R. Yeh. While smoke evacuators like that described in the foregoing patent have received widespread acceptance, they may nonetheless operate at less than maximum efficiency in the collection and removal from the surgical site of smoke and surgical debris. One of the reasons that smoke evacuator techniques heretofore used have not been optimally efficient is because the nozzle of the smoke evacuator, in most applications, must be located within approximately two inches of the surgical site.

Otherwise, there is a risk that substantial portions of the smoke and debris thus generated may dissipate into the atmosphere from the surgical site, posing health hazards to health care workers. Indeed, such electrosurgery and laser surgery techniques, because they tend to disburse blood into an aerosol, leave behind such aerosols which can pose a health risk to anyone entering the theater of the surgical operation, even several hours after the surgery has been completed. As will be appreciated by those skilled in the art, such surgical debris, including the blood aerosols above referred to, may contain pathogenic organisms, and particularly viruses. It is important that such debris be collected and removed from the environment as completely as possible.

It is accordingly an object of the present invention to provide improved apparatus for collecting and removing, with maximum efficiency, smoke and other surgical debris generated as a result of electrosurgical and laser surgical techniques.

It is a more specific object of the present invention to provide apparatus for the collection and removal of smoke and surgical debris in which substantially all of the smoke and surgical debris can be collected and removed from the environment.

It is a more specific object of the invention to provide apparatus for the collection and removal of smoke and surgical debris which can be used to efficiently collect such smoke and debris when used in combination with electrosurgery and laser surgery instruments.

These and other objections and advantages of the invention will appear more fully hereinafter with a description of the present invention.

SUMMARY OF THE INVENTION

The concept of the present invention recites a new and improved system for use with electrosurgical and laser surgical techniques in which a source of rapidly moving fluid under pressure is introduced to a surgical site and an exhaust or collection element operating under reduced pressure is likewise positioned adjacent the surgical site so that the rapidly moving fluid entrains substantially all of the smoke and debris in the rapidly moving gas stream for collection in the collection element.

It has been found that the use of the combination of a moving fluid under pressure to entrain smoke and debris into a rapidly moving air stream for collection by a collection element operating under a reduced pressure obviates the need to precisely control the proximity of the collection system to the surgical site. In other words, the use of vectored gas flow to direct the smoke and debris into a collection element makes it unnecessary that a nozzle be positioned within two inches of the surgical site as has been characteristic of the prior art.

In the preferred practice of the invention, the collection is configured so as to direct the entrained smoke and debris into a collection nozzle by means of a flared horn, and preferably a flared horn having the capability of an acoustical amplifier. It has been found that such flared configuration makes it possible to more completely collect the smoke and debris entrained in the rapidly moving fluid stream.

As used herein, the term "fluid" is intended to use and include fluid streams generally, including both gases and liquids. In the most preferred practice of the invention, however, it has been found that it is particularly efficient to use a rapidly moving air stream which is used to entrain from the surgical site smoke and other debris and direct that smoke and debris entrained in the moving air stream into the collection nozzle. It will be understood, however, that other gases may likewise be used such as nitrogen, carbon dioxide and like gases which are unreactive under the conditions existing at the surgical site.

DESCRIPTION OF THE DRAWINGS

FIG. 2 is a cross-sectional view of a preferred collection nozzle which may be employed in the practice of the invention.

FIG. 3 is a view taken along the lines of 3—3.

FIG. 4 is a perspective view of the collection nozzle illustrated in FIG. 2.

FIG. 8 is a schematic illustration of an alternate embodiment of the present invention.

DETAILED DESCRIPTION OF THE INVENTION

Figure 1:
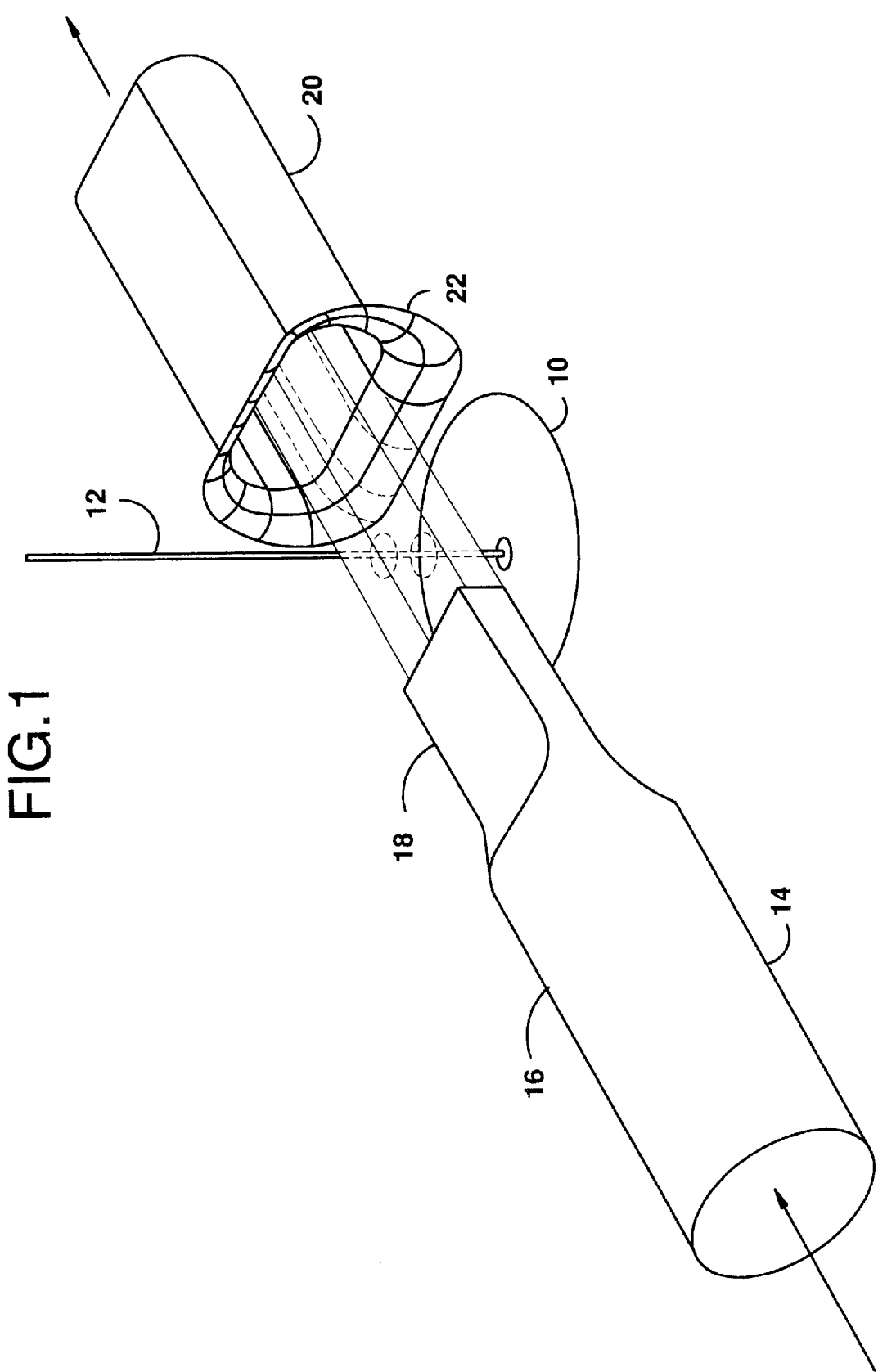
FIG. 1 is a schematic illustration of an apparatus embodying the features of the invention.

Referring now to FIG. 1 for a detailed description of the smoke evacuation apparatus of the invention, there is illustrated in that figure, a surgical site 10 on which there is focused a laser beam 12 generated by a medical laser device for performing, for example, dermatologic surgery. The laser probe itself is not illustrated in the drawings for purposes of simplicity, but it will be understood that such laser probes are well known to those skilled in the art. Such laser probes are themselves known to the art, and are offered for sale by, for example, Coherent Inc, Sarplan or Laserscope.

Positioned adjacent to surgical site 10 is a fluid pressure nozzle 14 having a generally cylindrical configuration 16 adapted to by connecting a source of fluid under pressure such as an air blower, not shown in the drawings for purposes of simplicity. The nozzle 14 terminates in a nozzle member 18 in its distal end. The configuration of nozzle portion 18 is not critical to the practice of the invention, and may be varied in accordance with well settled principles. It is preferred, however, that the nozzle portion 18 having a reduced cross-section to insure that the air discharged therefrom is discharged at a high fluid velocity. While the particular fluid velocity depends on the application, it has been found that fluid velocities in excess of 5 feet per second may be effectively used in the collection and entrainment of smoke and other surgical debris from the surgical site. And it will be appreciated by those skilled in the art, that it is also possible, and some times desirable, that even higher fluid velocities be used including those in excess of 100 feet per second.

Also positioned adjacent the surgical site is a collection nozzle 20 which is adapted to be connected to a source of reduced pressure such as a vacuum pump or an exhaust fan to reduce the pressure within the collection nozzle 20. That in turn insures that the fluid stream discharged from the nozzle portion 18 of the discharge nozzle 14 is not only directed toward the collection nozzle 20, but that the pressure existing in the collection nozzle 20 is low enough to rapidly collect all of the air discharged from the nozzle portion 18 having entrained within it smoke and other debris from the surgical site.

As will be appreciated by those skilled in the art, the use of the high pressure fluid nozzle in combination with the collection nozzle makes it possible to efficiently collect substantially all of the smoke and other airborne debris generated at the surgical site since that smoke and debris is entrained in the rapidly moving fluid stream discharged from nozzle portion 18. In a preferred embodiment of the invention, the cross sectional area of the collection nozzle is greater than the cross sectional area of the nozzle portion 18; that ensures laminar flow to the extent possible, which in turn ensures that substantially all of the rapidly moving air stream having a smoke and surgical debris entrained therein will be received and drawn into the collection nozzle 20.

In the most preferred practice of the invention, the collection nozzle 20 is preferably equipped with flared horn element 22 having the capability of operating as an acoustical amplifier. It has been found in accordance with the practice of the present invention, that the flared horn configuration 22 of the collection nozzle 20 maximizes the fluid stream collected by the collection nozzle 20.

In the absence of the flared element 22, the collection nozzle would simply be characterized as having a sharp edge having the capability of developing turbulence in the form of vortices in the vicinity of the edges of the nozzle. That in turn results in non-adiabatic compression of the fluid stream about the nozzle, resulting in an overall decrease in the efficiency of the induction of the fluid stream into the collection nozzle 20. When, however, the collection nozzle 20 is provided with a flared horn configuration 22 as illustrated in FIG. 1, the area of influx of the fluid stream from behind the nozzle is substantially eliminated. That in turn reduces the area from which air is inducted into the nozzle 20.

In the most preferred practice of the invention, the flared horn configuration of the nozzle is preferably hyperbolically configured. That in turn facilitates laminar flow of the fluid stream as it is inducted into the collection nozzle 20 while avoiding turbulence or vortices that otherwise interfere with the efficient induction of the fluid stream containing entrained smoke and other debris into the collection nozzle 20.

Figure 6:
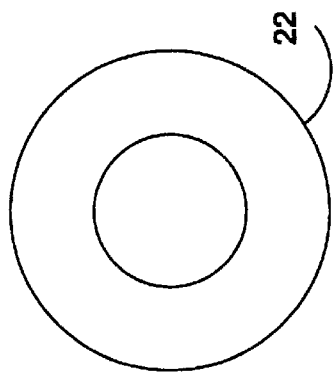
FIG. 6 is a view taken along the lines of 6—6 in FIG. 5.
Figure 5:
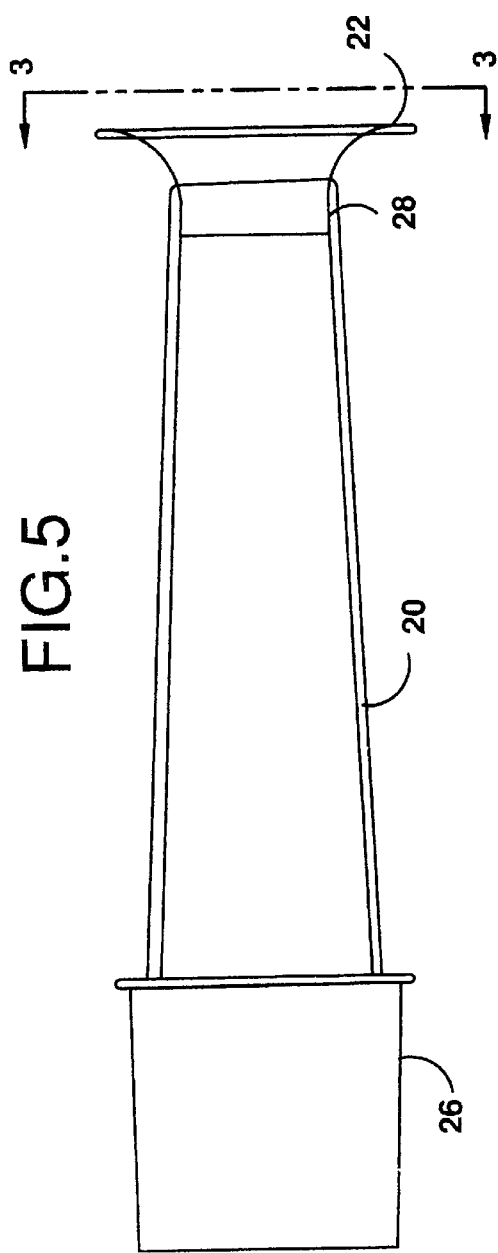
FIG. 5 is a side view and illustration of another collection nozzle embodying the features of the invention.
Figure 7:
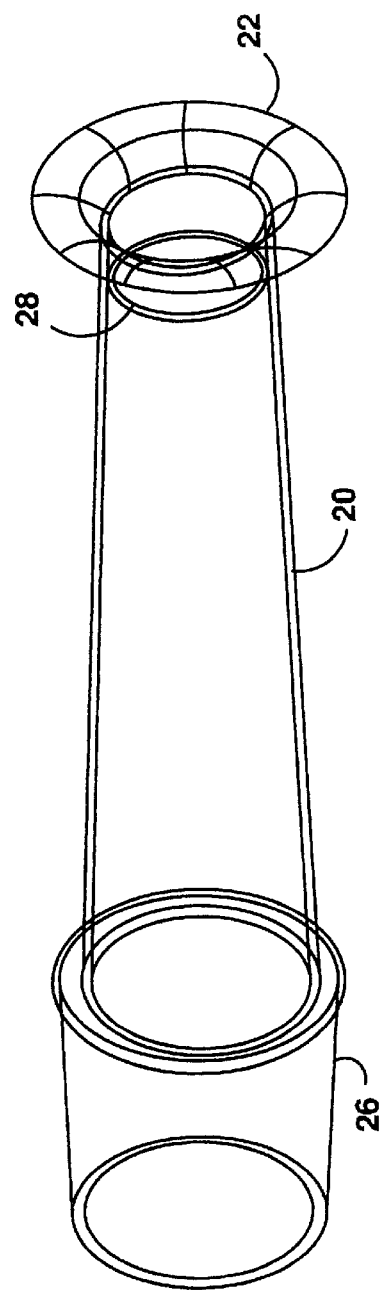
FIG. 7 is a perspective view of the collection nozzle illustrated in FIGS. 5 and 6.

Various forms of the collection nozzle 20 may be used as illustrated in FIGS. 2–4 and FIGS. 5–7, respectively. As shown in FIGS. 2–4, the collection nozzle 20 includes a body portion 24 on which there is mounted a horn nozzle element 22 through which the fluid stream containing entrained smoke and debris is inducted. The collection nozzle 20 also contains connector 26 to which there may be attached a hose leading to either an exhaust fan or a vacuum pump to establish the reduced pressure within the collection nozzle 20. While FIGS. 2–4 illustrate the horn as having an internal diameter 28 less than the internal diameter of the collection nozzle 24, it is also possible, as shown in FIGS. 5–7 of the drawings, that the collection nozzle may be dimensioned to correspond to the minimum diameter 28 of the acoustical horn 22.

As will be appreciated by those skilled in the art, it is also possible, and some times highly desirable, to integrate the smoke evacuation apparatus of the present invention with the probe or hand piece of a laser instrument so that the discharge nozzle and the collection nozzle are integrated with the laser beam emitter or handpiece to thereby insure maximum collection of the fluid stream containing entrained smoke and other debris. An illustration of this concept of the present invention is illustrated in FIG. 8 of the invention where there is shown a substantially cylindrical laser hand piece 30 having at its distal end a lens 32 from which the laser beam 12 emanates. Such hand pieces or probes are, as indicated, conventionally used in laser surgery apparatus.

Positioned about the periphery of the probe 30 are a pair of tubes 34 and 36; the tube 34 is connected to a source of fluid under pressure such as an air blower, likewise not shown in the drawings, to deliver the fluid under pressure to a discharge nozzle 38. As illustrated in FIG. 8, the discharge nozzle 38 is positioned so as to direct the fluid under pressure discharged therefrom substantially transversely across the laser beam and substantially parallel to the lens 32. The other tube 36 is connected to a source of reduced pressure such as an exhaust fan or a vacuum pump, likewise not shown in the drawings for purposes of simplicity, to collect the air discharged from the nozzle 38. The collection tube 36 is preferably equipped with a flared or horned collection nozzle 40 adjacent the discharge nozzle 38.

In that way, the air discharged under pressure from the discharge nozzle 38 is swept across the lens 32 of the probe 30 to entrain smoke and other debris in the rapidly moving fluid stream which is then collected by the collection nozzle 40 for discharge through the collection tube 36 for a source of reduced pressure.

In addition, the configuration of this embodiment of the invention continuously directs clean air parallel to and across the lens 32. That has the further advantage of clearing smoke and surgical debris from the surgical site, thereby preventing the build-up of such smoke and debris on the lens itself. Thus, in the practice of this embodiment, it is not necessary to clean the handpiece lens as often as has been required in the past.

As will be appreciated by those skilled in the art, the integration of the discharge nozzle with the collection nozzle with the probe itself has the advantage of allowing a physician using the probe to control the movement of the discharge nozzle 38 and the collection nozzle 40 with the movement of the probe 30, all in one operation. It is thus unnecessary to separately move the discharge nozzle and the collection nozzle when the laser beam is repositioned during the course of laser surgery.

While FIG. 8 illustrates the discharge nozzle and the collection nozzle as integral with a fixed nozzle to the probe 30, it will be understood that it is likewise possible, and some times desirable, to slidably mount the discharge tube 34 and the collection nozzle 36 on the probe 30 to permit the positioning of the discharge nozzle 38 and the collection nozzle 40 with respect to the lens 32 from the laser beam 12 emanates.

It will be understood that various changes and modifications can be made in the details of configuration and use without departing from the spirit of the invention as will be especially defined in the following claims.

What is claimed is:

1. A smoke evacuator for use in removing smoke comprising:
   (a) a fluid nozzle positioned adjacent to a laser target site and adapted to supply a rapidly moving fluid stream to entrain smoke in the rapidly moving fluid stream to thereby remove the smoke from the site;
   (b) a flared horn collection nozzle positioned adjacent to the site and positioned to receive the rapidly moving fluid stream having smoke entrained therein; and
   (c) an evacuation means operatively connected to the collection nozzle in fluid flow communication therewith, said evacuation means creating a reduced pressure in the collection nozzle whereby substantially all the rapidly moving fluid stream having smoke entrained therein is drawn into the collection nozzle to remove the smoke from the environment, wherein the collection nozzle has a greater cross sectional area than the fluid nozzle.

2. The smoke evacuator as defined in claim 1 wherein the flared horn portion has hyperbolic configuration.

3. The smoke evacuator as defined in claim 1 wherein the fluid nozzle includes a generally cylindrical portion and the nozzle portion having a cross sectional area less than the cross sectional area of the cylindrical portion so that fluid discharged from the nozzle portion has a greater linear velocity than that of fluid introduced to the collection nozzle.

4. A probe for use with a laser with evacuates smoke from a site adjacent to the laser comprising:
   (a) a laser hand piece including means for generating a laser beam and a lens mounted at the distal end of the laser hand piece whereby the laser beam emanates through the lens; and;
   (b) a tubular member mounted on the hand piece to direct a fluid stream across the lens to entrain smoke in the fluid stream;
   (c) a flared horn collection tube mounted on the hand piece and positioned to collect the fluid stream having entrained therein smoke, said collection tube adapted to be maintained at a reduced pressure whereby substantially all the rapidly moving fluid stream having smoke entrained therein is drawn into the collection nozzle to remove the smoke from the environment, wherein the collection tube has a greater cross sectional area than the tubular member.

5. The probe as defined in claim 4 wherein the flared horn portion has a hyperbolic configuration.

6. The probe as defined in claim 4 wherein the tubular member includes a nozzle portion to direct the fluid stream across the lens to entrain smoke and surgical debris therein.

7. The probe as defined in claim 4 which includes evacuation means operatively connected to the collection tube in fluid flow communication and with the evacuation means operating to reduce the pressure in the collection tube to thereby draw the rapidly moving fluid stream having smoke entrained therein into the collection tube.

* * * * *